(12) United States Patent
Sheng (10) Patent No.: US 9,439,719 B2
(45) Date of Patent: Sep. 13, 2016

(54) OPERATION HANDLES FOR ELECTROCAUTERY

(71) Applicant: GETAC TECHNOLOGY CORPORATION, Hsinchu County (TW)

(72) Inventor: Yen-Long Sheng, Taipei (TW)

(73) Assignee: Getac Technology Corporation, Hsinchu County (TW)

( * ) Notice: Subject to any disclaimer, the term of this patent is extended or adjusted under 35 U.S.C. 154(b) by 385 days.

(21) Appl. No.: 14/274,631

(22) Filed: May 9, 2014

(65) Prior Publication Data

US 2015/0320484 A1 Nov. 12, 2015

(51) Int. Cl.
| | |
|---|---|
| A61B 1/00 | (2006.01) |
| A61B 18/14 | (2006.01) |
| A61B 19/00 | (2006.01) |
| A61B 17/29 | (2006.01) |
| A61B 17/00 | (2006.01) |
| A61B 18/00 | (2006.01) |

(52) U.S. Cl.
CPC ....... *A61B 18/1445* (2013.01); *A61B 17/2909* (2013.01); *A61B 19/22* (2013.01); *A61B 2017/0042* (2013.01); *A61B 2017/00438* (2013.01); *A61B 2017/2911* (2013.01); *A61B 2017/2946* (2013.01); *A61B 2018/0091* (2013.01); *A61B 2018/00595* (2013.01); *A61B 2018/00922* (2013.01); *Y10T 74/20396* (2015.01)

(58) Field of Classification Search
CPC .............. A61B 18/1445; A61B 19/22; A61B 2017/00438; A61B 2017/0042; A61B 2018/00922; A61B 2018/00595
See application file for complete search history.

(56) References Cited

U.S. PATENT DOCUMENTS

| | | | |
|---|---|---|---|
| 6,193,718 B1 * | 2/2001 | Kortenbach | A61B 18/1445 606/45 |
| 2010/0069903 A1 * | 3/2010 | Allen, IV | A61B 17/2816 606/45 |
| 2011/0306952 A1 * | 12/2011 | Chen | A61B 17/29 606/1 |
| 2012/0004652 A1 * | 1/2012 | Moua | A61B 18/1206 606/33 |
| 2013/0023911 A1 * | 1/2013 | Esanu | A61B 17/122 606/158 |
| 2015/0320484 A1 * | 11/2015 | Sheng | A61B 18/1445 74/491 |
| 2015/0331443 A1 * | 11/2015 | Lamser | G05G 5/005 74/532 |

FOREIGN PATENT DOCUMENTS

| | | |
|---|---|---|
| CN | 101035482 A | 9/2007 |
| TW | M428027 | 5/2012 |

* cited by examiner

*Primary Examiner* — David M Fenstermacher (57) ABSTRACT

An operation handle for electrocautery includes: a grip, an operation rod, a stopping part, a positioning bar, and a driven member. One end of the operation rod is jointly connected to the grip, and the other end has a pressing portion. The operation rod moves selectively from an initial position to at least one work position. The stopping part is disposed on the operation rod and adjacent to the pressing portion. The positioning bar is disposed on the grip and comprises at least one positioning groove. When the pressing portion of the operation rod is forced, the operation rod moves from the initial position to the at least one work position, and one end of the driven member is lodged in the at least one positioning groove.

9 Claims, 9 Drawing Sheets

OPERATION HANDLES FOR ELECTROCAUTERY

BACKGROUND

1. Technical Field

The present invention relates to operation handles, and more generally to operation handles for electrocautery.

2. Related Art

During surgical operations, it is common to use surgical instruments such as scissors and jaw members to cut or clamp a patient's tissues. It is also common to use surgical instruments such as electrosurgical instruments for cutting, sealing or stopping bleeding of an affected part or a wound. Currently, there are many surgical instruments, such as electrocautery, with handles for doctors to operate intuitively when cutting or clamping.

Figure 1:
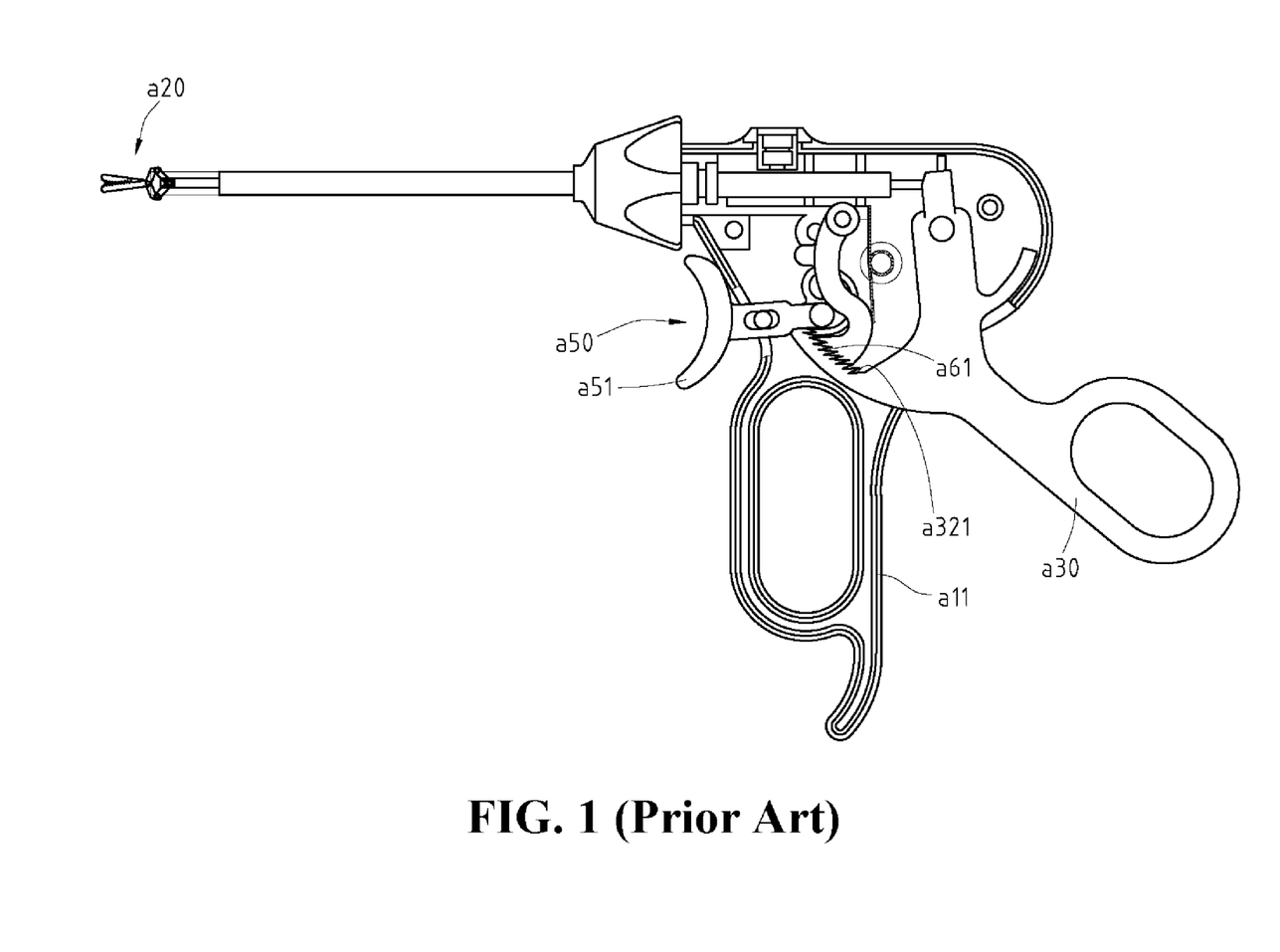
FIGS. 1-2 are schematic diagrams of a traditional surgical instrument in different status.
Figure 2:
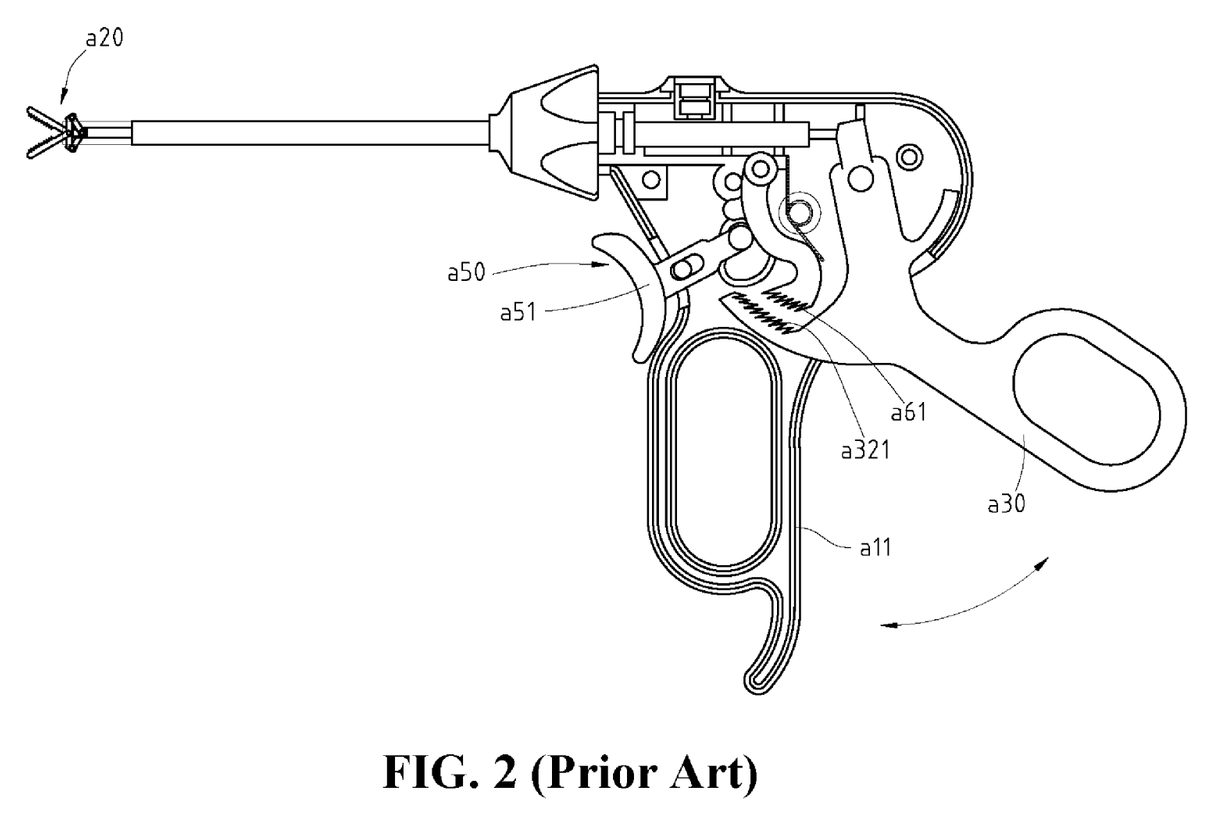

FIGS. 1 and 2 show surgical instruments with jaw members. When a doctor wants to use jaw members a20 to clamp something, they may pull the second handle a30 close to the handle all. Meanwhile, the positioning cogs a321 and the locking cogs a61 are engaged with each other, so the second handle a30 may be locked at a fix position for the jaw members a20 to clamp something. At the same time, even if the doctor's hand is away from the second handle a30 and the handle all, the jaw members a20 continue clamping by the engagement of the positioning cogs a321 and the locking cogs a61.

When the doctor wants to release the clamping, they must press a pressing part a51 of a controlling element a50, so the locking cogs a61 may be released from the positioning cogs a321. At the same time, the doctor must move the second handle a30 away from the handle all. During an operation, four fingers of the doctor may be located at the handle all and the thumb may be located at the second handle a30 for the engagement by pulling the second handle a30. However, under the engagement release, one forefinger or one middle finger must press the pressing part a51. That is, the pressing part a51 is pressed toward to the second handle a30. However, the other three fingers remain located at the handle all to hold the handle all. At the same time, the thumb, located at the second handle a30, must move the second handle a30 backward away from the handle all.

As a result, the doctor must use one finger pressing forward and the other finger moving backward. Mastering such a release procedure requires repeated practice. Consequently, when the doctor first uses this kind of instrument, the learning curve required to develop skill with the instrument is high.

SUMMARY

Accordingly, the present invention provides an operation handle for electrocautery comprising: a grip, an operation rod, a stopping part, a positioning bar, and a driven member. The operation rod has two ends, one end is jointly connected to the grip, and the other end has a pressing portion. The operation rod moves selectively from an initial position to at least one work position. The stopping part is disposed on the operation rod and adjacent to the pressing portion. The positioning bar is disposed on the grip and comprises at least one positioning groove. The driven member comprises a driven rod and a torsional spring, wherein the driven rod is jointly connected to the operation rod and adjacent to the pressing portion. An end of the torsional spring is disposed against the operation rod, and another end of the torsional spring is selectively disposed against the driven rod. The torsional spring pushes against the driven rod so as to allow an end of the driven rod selectively stopping against the stopping part. When the pressing portion of the operation rod is forced, the operation rod moves from the initial position to the at least one work position, and another end of the driven rod is lodged in the at least one positioning groove.

When a doctor is in an operation, their thumb is located in the pressing portion, and their other four fingers are located in the grip. The thumb presses the pressing portion so as to move the operation rod from the initial position to the work position. The initial position may be release position, and the work position may be in clamping position. When the operation rod is located at the work position by pressing the pressing portion, one end of the driven rod is lodged in any one of the positioning grooves of the positioning bar. Whereby, the operation rod is fixed at the work position as required. Consequently, when the hand of the doctor is away from the grip and the operation rod, the operation rod maintains the work position, so the electrocautery may maintain working status or clamping status.

When the doctor wants to release the working status or clamping status, they may only need to move the operation rod away from the grip, i.e. their thumb presses the operation rod away from the grip. Consequently, it may allow the doctor to use the operation handles as scissors without any further practice or a lengthy learning curve. Accordingly, the doctor may be skilled to the operation handle promptly, without thinking about releasing the clamping status.

It is to be understood that both the foregoing general description and the following detailed description presented below are intended to provide an overview or framework for understanding the nature and character of the disclosure as it is claimed. The accompanying drawings are included to provide a further understanding of the disclosure, and are incorporated into and constitute a part of this specification. The drawings illustrate various embodiments of the disclosure, and together with the description serve to explain the principles and operations of the disclosure.

DETAILED DESCRIPTION

Reference is now made in detail to various embodiments of the disclosure, examples of which are illustrated in the accompanying drawings. Whenever possible, the same or like reference numbers and symbols are used throughout the drawings to refer to the same or like parts. The drawings are not necessarily to scale, and one skilled in the art will recognize where the drawings have been simplified to illustrate the key aspects of the disclosure.

Figure 3:
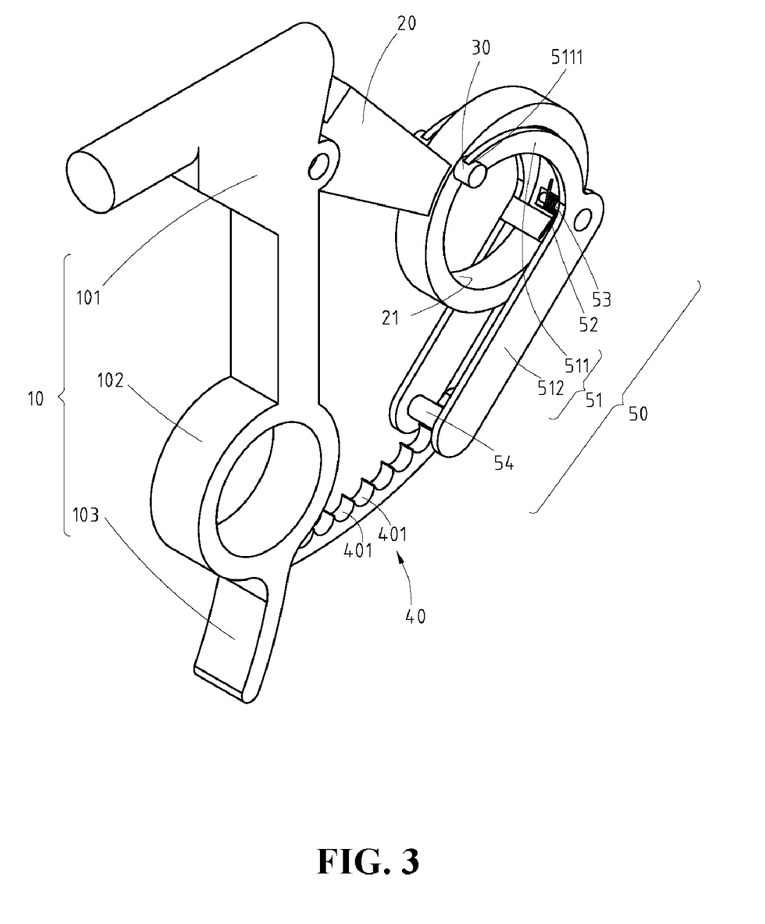
FIG. 3 is schematic diagram of an operation handle in accordance with a first embodiment of the present invention.
Figure 4:
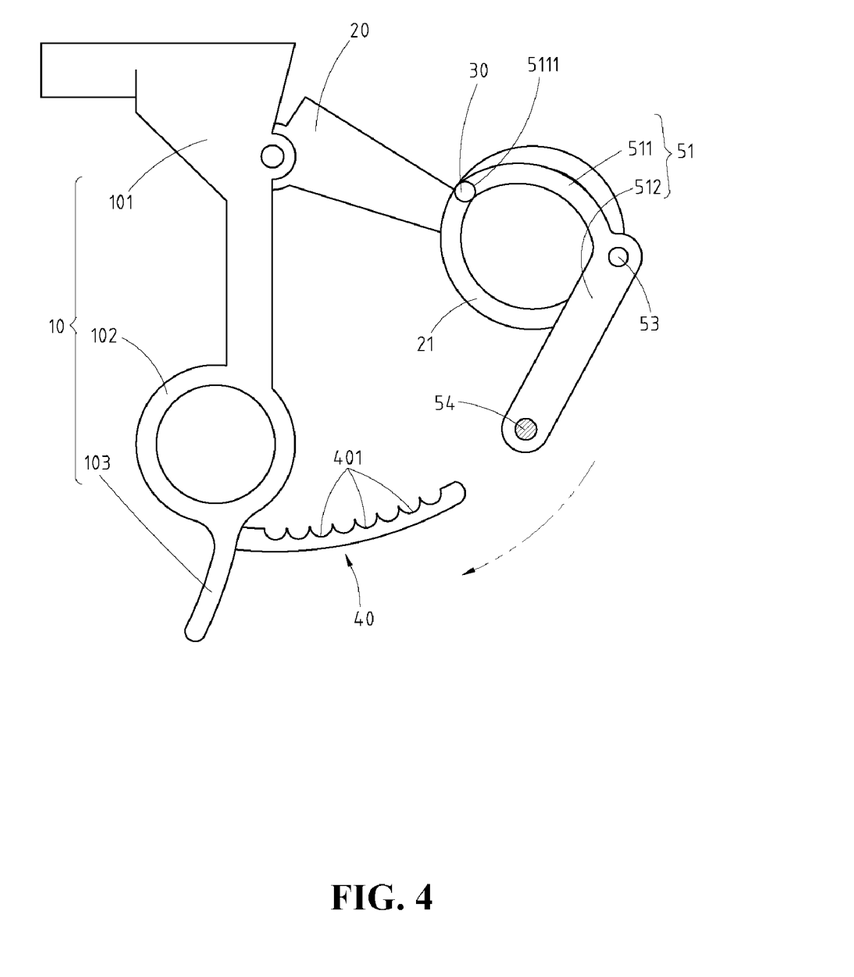
FIG. 4 is a side view of the operation handle in accordance with the first embodiment of the present invention.

Please refer to FIGS. 3 and 4, which respectively show a schematic diagram and a side view of an operation handle in accordance with a first embodiment of the present invention. The operation handle of the present invention comprises a grip 10, an operation rod 20, a stopping part 30, a positioning bar 40, and a driven member 50. The grip 10 comprises a body 101, a finger ring 102, and a finger rest part 103. One end of the body 101 connects to an element of surgical instrument such as electrocautery, clamping instrument, etc. The other end of the body connects to the finger ring 102. The finger rest part 103 connects to the finger ring 102 in opposite direction to the body 101. The body 101 and the finger rest part 103 are respectively connected to the finger ring 102 in opposite direction. When in use, a doctor may put the third finger through the finger ring 102, put the forefinger and the middle finger on the body 101 above the finger ring 102, and put the little finger on the finger rest part 103. Thus, the handling of the operation handle may be more smoothly and conveniently.

One end of the operation rod 20 is jointly connected to the grip 10, and the other end has a pressing portion 21. The pressing portion 21 may be shaped as a round ring. The big thumb may be put into the round ring and press the inner wall of the round ring. The stopping part 30 is disposed on the operation rod 20 and adjacent to the pressing portion 21. In the present embodiment, the stopping part 30 is a pillar, as shown in FIG. 3. However, in other embodiments, the stopping part 30 may be a pillar with any geometric shape so as to allow an end of the driven rod 50 selectively stopping against the stopping part 30. The details of the driven member 50 are described below.

The positioning bar 40 is disposed on the finger ring 102 of the grip 10, comprising at least one positioning groove 401. As shown in FIG. 4, the positioning bar 40 extends outward from the connection of the finger ring 102 and the finger rest part 103 with an arc that is arcing with a center at the jointly connection of the grip 10 and the operation rod 20. Thus, the positioning bar 40 is substantially shaped as a long arc. When the pressing portion 21 of the operation rod 20 moves close to the finger ring 102 at a fixed work position, the pressing portion 21 touches against the finger ring 102, but not touching with the positioning bar 40. The number of the positioning groove 401 may be designed as required for the clamping degrees. In the present embodiment, the positioning grooves 401 are shaped continuously in multi-semicircle tubular.

The driven member 50 comprises a driven rod 51 and a torsional spring 52. The driven rod 51 is jointly connected to the operation rod 20 and adjacent to the pressing portion 21. An end of the torsional spring 52 is disposed against the operation rod 20, and another end of the torsional spring 52 is selectively disposed against the driven rod 51. As shown in FIG. 3, a shaft 53 may be used for connecting the torsional spring 52 and the driven rod 51 to the pressing portion 21 of the operation rod 20 at the inner wall of the round ring. Thus, due to the torsion of the torsional spring 52, an end of the driven rod 51 selectively stopping against the stopping part 30.

As shown in FIGS. 3 and 4, the driven rod 51 comprises a first rod 511 and a second rod 512. The first rod 511 and the second rod 512 are connected and formed substantially as L-shape. In the present embodiment, in order to move the driven rod 51 more smoothly, there are two driven rod 51 disposed in parallel at two sides of the operation rod 20 and jointly fixed by the shaft 53. However, in other embodiment, there may be used with only one driven rod 51.

An open end of the first rod 511 is selectively disposed against the stopping part 30. In order to properly dispose the first rod 511 of the driven rod 51 against the stopping part 30, the open end of the first rod 511 comprises a recessed portion 5111 corresponding to the shape of the stopping part 30. For example, the stopping part 30 is a pillar, and the recessed portion 5111 corresponds to the shape of the pillar.

Please refer to FIG. 3, in which the open end of the second rod 512 is selectively lodged in the positioning groove 401. In this embodiment, the second rod 512 of the driven rod 51 comprises a positioning cylinder 54 shaped as a pillar, which is corresponding to the shape of the positioning groove 401. Thus, the positioning cylinder 54 may be fixed temperately into the positioning groove 401. When the operation rod 20 moves to the work position, the positioning cylinder 54 is lodged in the semicircle tubular positioning groove 401.

Figure 5:
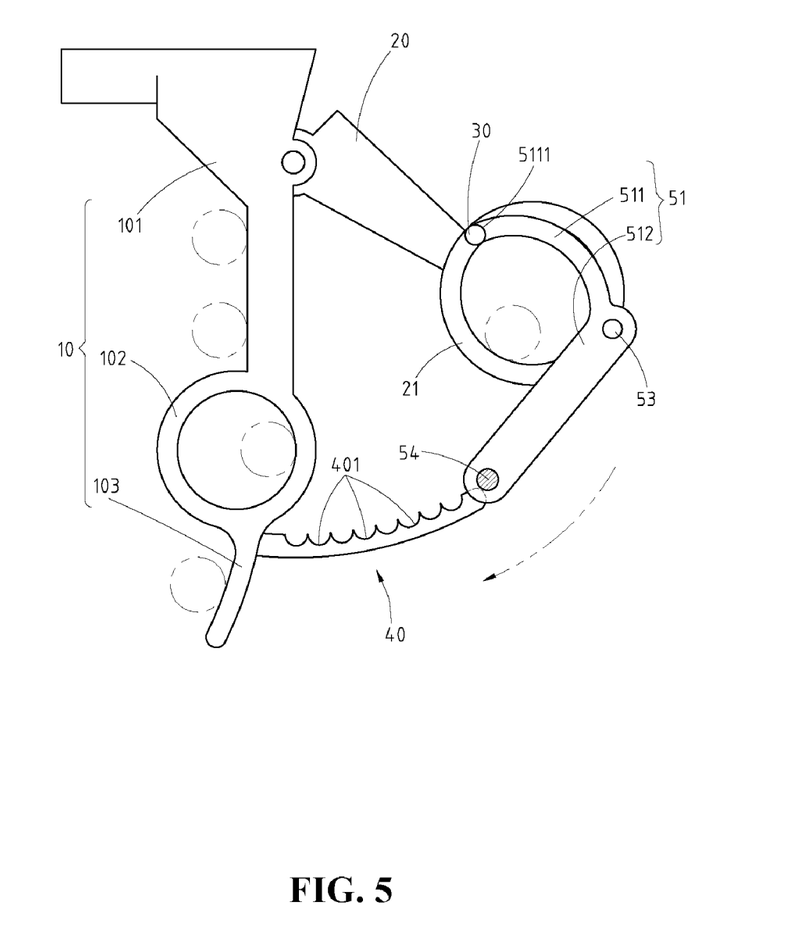
FIGS. 5-9 are a side views of the operation handle in accordance with the first embodiment of the present invention showing the movement of the operation handle.

Please refer to FIGS. 5-9, which show the movement of the operation handle in accordance with the present invention. As shown in FIG. 5, when in use, at the beginning, the user put the big thumb in the pressing portion 21, the third finger in the finger ring 102, the forefinger and the middle finger on the body 101, and the little finger on the finger rest part 103.

Figure 9:
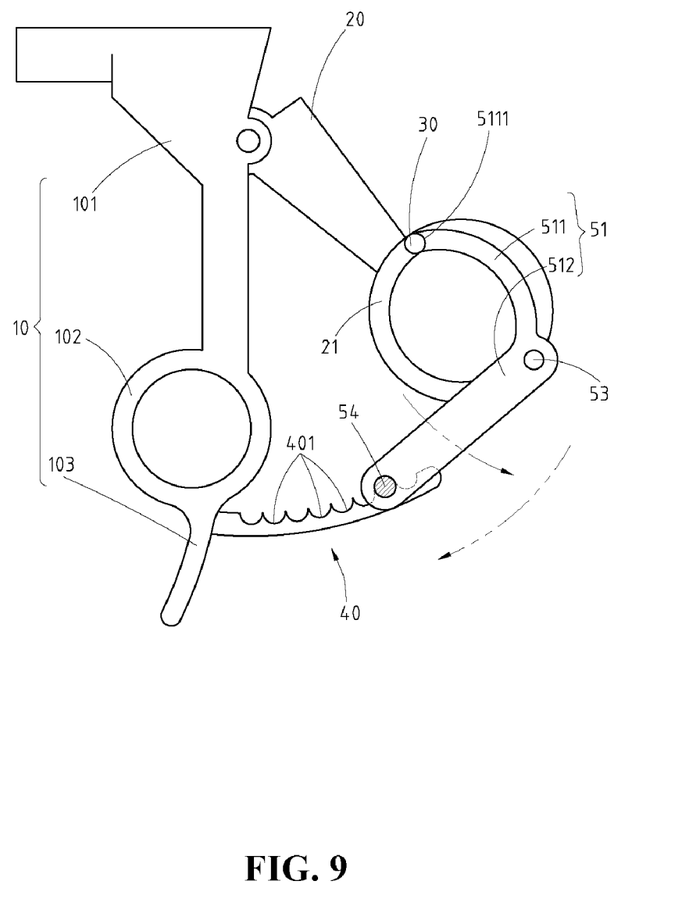

The user presses the pressing portion 21 of the operation rod by the big thumb, and then the operation rod 20 moves accordingly from an initial position to at least one work position. The initial position means, as shown in FIG. 4, the status showing the positioning cylinder 54 of the second rod 512 of the driven rod 51 not touching with the positioning bar 40. Or, the initial position means, as shown in FIG. 5, the status showing positioning cylinder 54 of the second rod 512 of the driven rod 51 is touching with an open end of the positioning bar 40. The work position means, as shown in FIG. 7 or FIG. 9, the positioning cylinder 54 of the second rod 512 of the driven rod 51 is lodged in any one of the positioning grooves 401.

Figure 6:
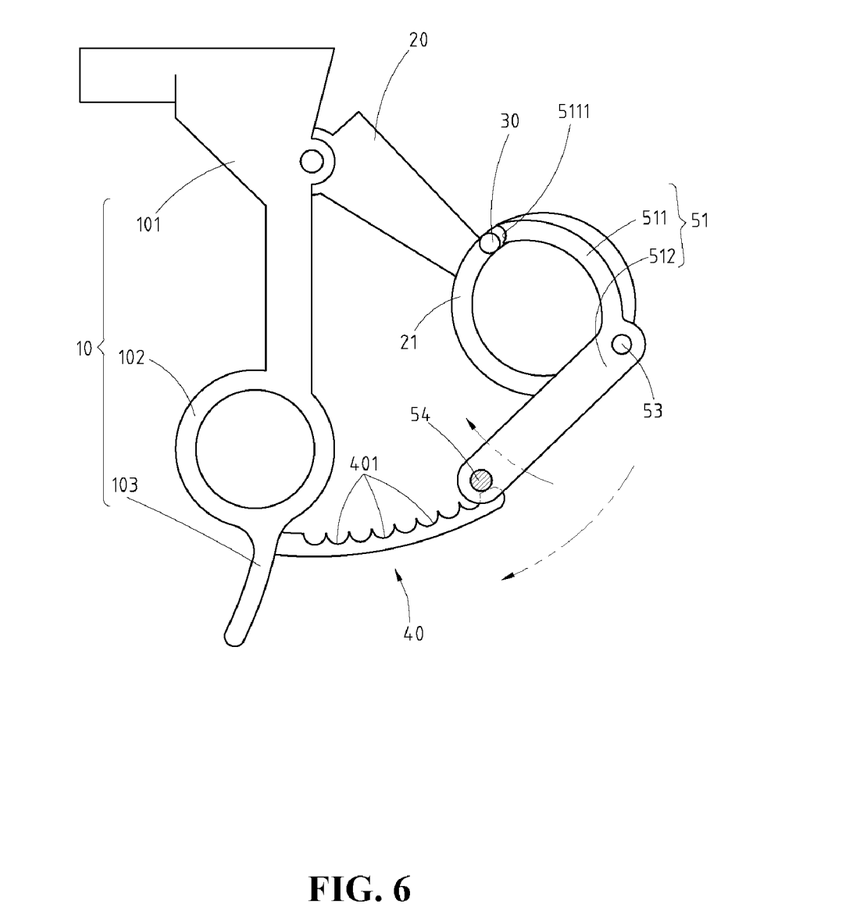

As shown in FIGS. 5 and 6, when the thumb presses the pressing portion 21 of the operation rod 20, the pressing portion 21 of the operation rod 20 moves close to the finger ring 102 of the grip 10. And the positioning cylinder 54 of the second rod 512 of the driven rod 51 touches the positioning bar 40. Further, the second rod 512 of the driven rod 51 is driven to rotate clockwise by the shaft 53. Meanwhile, the first rod 511 connected with the second rod 512 is also driven to rotate clockwise by the shaft 53. The recessed portion 5111 of the first rod 511 of the driven rod 51 is away from the stopping part 30.

Figure 7:
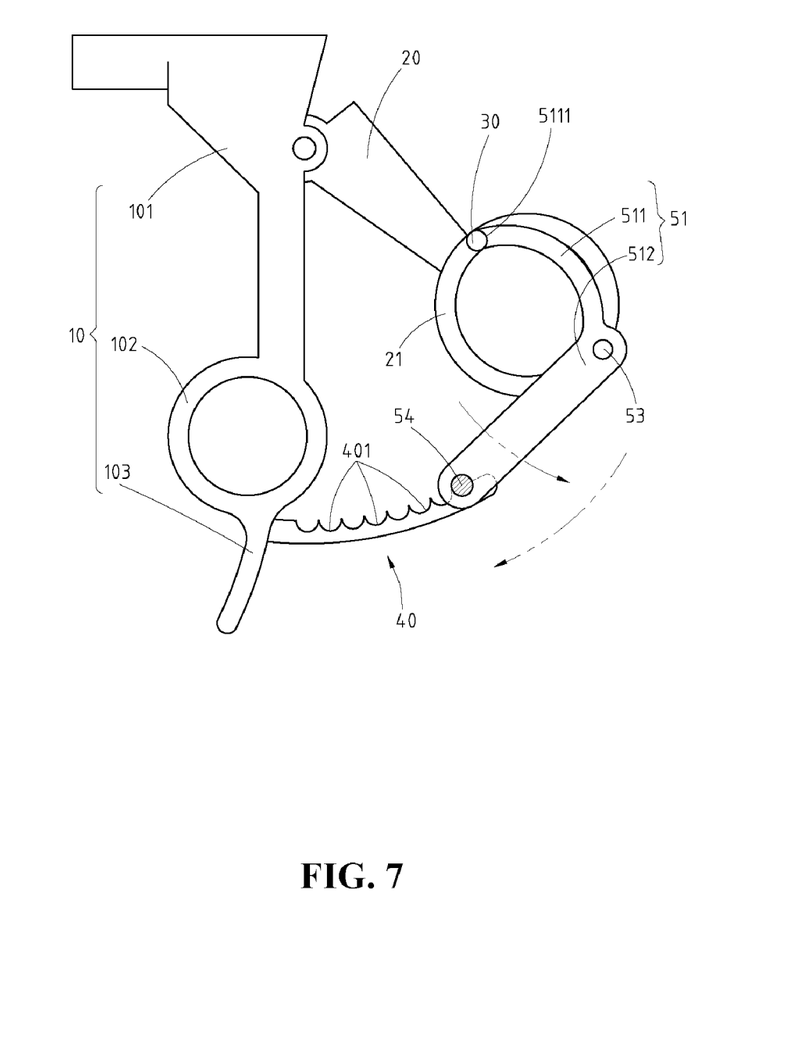

Please refer to FIG. 7, in which when the thumb continuously presses the pressing portion 21 of the operation rod 20, the positioning cylinder 54 of the second rod 512 of the driven rod 51 is pushed to be lodged in one positioning groove 401. At the same time, the torsional spring 52 provides torsion for the driven rod 51 to rotate anticlockwise, so the positioning cylinder 54 of the second rod 512 of the driven rod 51 is lodged in one positioning groove 401 and the recessed portion 5111 at the open end of the first rod 511 of the driven rod 51 is engaged with the stopping part 30.

When the operation handle comes to the work position for operation such as electrosurgical or clamping procedure, the work position may be kept. Further, the doctor (or user), may leave the operation handle to proceed with other necessary operations. Due to the torsion of the torsional spring 52, the positioning cylinder 54 of the second rod 512 is firmly lodged in the positioning groove 401. Even though the fingers of the user are moved away from the operation handle, the operation handle can be kept in the work position without releasing or moving.

When the doctor finishes the electrosurgical or clamping procedure, the operation handle should be released from the clamping or electrosurgical procedure, from the work position to the initial position, as shown in FIG. 7 to FIG. 5. That is, the thumb of the user presses the operation rod 20 moving from the work position to the initial position. Meanwhile, the positioning cylinder 54 of the second rod 512 of the driven rod 51 is moved away from the positioning groove 401. Due to the interaction between the positioning cylinder 54 of the second rod 512 and the positioning bar 40, the second rod 512 of the driven rod 51 is driven to rotate clockwise by the shaft 53 and the recessed portion 5111 at the open end of the first rod 511 of the driven rod 51 is driven away from the stopping part 30.

When the user presses continuously on the operation rod 20, as shown in FIG. 5, the positioning cylinder 54 of the second rod 512 of the driven rod 51 is totally away from the positioning bar 40 or is touching with the open end of the positioning bar 40. At the same time, the force from the interaction provided by the positioning bar 40 is lapsed, so the torsional spring 52 provides torsion for the driven rod 51 to rotate anticlockwise and the recessed portion 5111 at the open end of the first rod 511 of the driven rod 51 is engaged with the stopping part 30 again.

Whereby, when the user is using with the operation handle in accordance with the present invention, no matter whether they want to clamp or to activate an electrosurgical procedure, to release the clamping or to stop electrosurgical procedure, it is very convenient for the user to use the operation handle as a scissor to clamp and open with fingers. When the grip 10 and the operation rod 20 are in the work position for clamping or activating the electrosurgical procedure, under the interaction between the driven member 50 and the positioning bar 40, no other gesture or further operation is needed to maintain clamping or continue the electrosurgical procedure. When in release, it is easy for the user to use the operation handle as the scissor to open by fingers moving outwardly, without any additional pressing or operating. The grip 10 and the operation rod 20 can be returned to the initial position from clamping or the electrosurgical procedure. Thus, according to the operation handle of the present invention, the user can use it as a scissor without any additional practice or learning curve. The user does not need to think about how to release the clamping or electrosurgical procedure.

Figure 8:
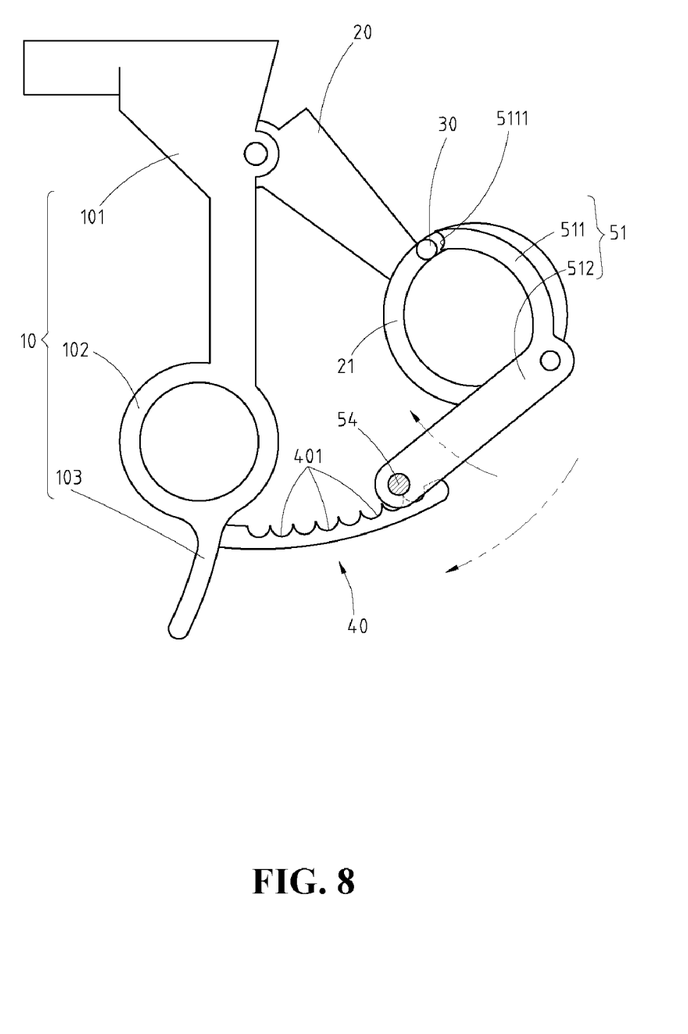

Please refer to FIGS. 7 to 9, in which when the pressing portion 21 of the operation rod 20 is under the work position as shown in FIG. 7, and if the user wants to clamp further firmly, they may keep pressing the pressing portion 21 of the operation rod 20. The interaction between the positioning bar 40 and the driven member 50, the positioning cylinder 54 of the second rod 512 of the driven rod 51 leaves the original positioning groove 401 and moves to another positioning groove 401. Under the torsion of the torsional spring 52, the positioning cylinder 54 is 1 firmly lodged in another positioning groove 401. Thus, when the user keeps pressing the pressing portion 21 of the operation rod, the work position moves from the original one to another without additional pressing or operating. The operation is therefore intuitive, and the user does not require any further practice or learning curve. The user may be skilled in a short time, and avoid any negligent operation due to inexperience.

It will be apparent to those skilled in the art that various modifications and variations can be made to the present disclosure without departing from the spirit and scope of the disclosure. Thus it is intended that the present disclosure cover the modifications and variations of this disclosure provided they come within the scope of the appended claims and their equivalents.

What is claimed is:

1. An operation handle for electrocautery comprising:
a grip;
an operation rod having two ends, one end being jointly connected to the grip and the other end having a pressing portion, wherein the operation rod moves selectively from an initial position to at least one work position;
a stopping part disposed on the operation rod, being adjacent to the pressing portion;
a positioning bar disposed on the grip, comprising at least one positioning groove; and
a driven member comprising a driven rod and a torsional spring, wherein the driven rod is jointly connected to the operation rod and adjacent to the pressing portion, an end of the torsional spring is disposed against the operation rod and another end of the torsional spring is selectively disposed against the driven rod, and the torsional spring pushes against the driven rod so as to allow an end of the driven rod selectively stopping against the stopping part;
when the pressing portion of the operation rod is forced, the operation rod moves from the initial position to the at least one work position, and another end of the driven rod is lodged in the at least one positioning groove.

2. The operation handle for electrocautery according to claim 1, wherein when the pressing portion of the operation rod is forced continuously, the operation rod moves from the one work position to another one work position, and the another end of the driven rod is lodged in another one positioning groove moved from the one positioning groove.

3. The operation handle for electrocautery according to claim 1, further comprising when the operation rod and the driven rod are forced simultaneously, the operation rod moves from the at least one work position back to the initial position such that the end of the driven rod gets away from the stopping part, and the another end of the driven rod gets away from the at least one positioning groove.

4. The operation handle for electrocautery according to claim 1, wherein the driven rod comprises a first rod and a second rod, the first rod and the second rod are connected and formed substantially as L-shape, an open end of the first rod is selectively disposed against the stopping part, and an open end of the second rod is lodged in the at least one positioning groove.

5. The operation handle for electrocautery according to claim 4, wherein the at least one positioning groove is shaped in semicircle tubular and the open end of the second rod comprises a positioning cylinder, when the operation rod moves to the at least one work position, the positioning cylinder is lodged in the semicircle tubular positioning groove.

6. The operation handle for electrocautery according to claim 4, wherein the stopping part is a pillar, and the open end of the first rod comprises a recessed portion corresponding to the shape of the pillar.

7. The operation handle for electrocautery according to claim 1, wherein the pressing portion is shaped as a round ring.

8. The operation handle for electrocautery according to claim 1, wherein the grip comprises a body, a finger ring, and a finger rest part, wherein the body and the finger rest part respectively connected to the finger ring in opposite direction.

9. The operation handle for electrocautery according to claim 8, wherein the positioning bar extends outward from the connection of the finger ring and the finger rest part with an arc that is arcing with a center at the jointly connection of the grip and the operation rod.

* * * * *